US00PP10571P

United States Patent [19]

VandenBerg

[11] Patent Number: Plant 10,571

[45] Date of Patent: Aug. 25, 1998

[54] CHRYSANTHEMUM PLANT NAMED 'RED AKRON'

[75] Inventor: Cornelis P. VandenBerg, Salinas, Calif.

[73] Assignee: Yoder Brothers, Inc., Barberton, Ohio

[21] Appl. No.: 786,419

[22] Filed: Jan. 21, 1997

[51] Int. Cl.[6] ..... A01H 5/00

[52] U.S. Cl. ..... Plt./82.5

[58] Field of Search ..... Plt./74.1, 82.5

[56] References Cited

U.S. PATENT DOCUMENTS

| | | | |
|---|---|---|---|
| P.P. 7,325 | 9/1990 | VandenBerg | Plt./82.5 |
| P.P. 8,292 | 7/1993 | VandenBerg | Plt./74.1 |
| P.P. 9,105 | 4/1995 | VandenBerg | Plt./74.1 |
| 4,616,099 | 10/1986 | Sparkes | 47/58 |

OTHER PUBLICATIONS

Broetjes, et al., 1980, "A Mutant of a Mutant of a . . . Irradication of Progressive Radiation–Induced Mutants in a Mutation Breeding Progamme With *Chrysanthemum morifolium*", Euphytica 29:525–530.

Gosling, ed., 1979, "the Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegetatively Propagates Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced By X–rays", Am. Soc. Hoit. Sci. Proc., pp. 613–620.

Broetjes, 1966, "Mutation Breeding of Chrysanthemums", Euphytica, 15: 156–162.

Dowrick, et al., 1966, "The Induction of Mutations in Chrysanthemum Using X–and Gamma Radiation", Euphytica, 15:204–210.

UPOU ROM—Plant Variety Database Mar. 1997, GTI Jouue Retrieval Software, 'Red Akron' Citation.

*Primary Examiner*—Howard J. Locker
*Attorney, Agent, or Firm*—Foley & Lardner

[57] ABSTRACT

A Chrysanthemum plant named Red Akron particularly characterized by its flat capitulm form; daisy capitulm type; dark red ray floret color; diameter across face of capitulm of 64 to 76 mm when fully opened, when grown as a pinched spray pot mum; photoperiodic flowering response of 50 to 56 days after start of short days; plant height, with 14 to 16 long days after sticking unrooted cuttings and with 1 to 2 applications of 2500 ppm B-9 SP ranges from 20 to 30 cm when grown as a pinched pot mum with 4 cuttings in a 15 cm pot; branching pattern is spreading and prolific, each plant developing 4 to 6 laterals after pinch; and recommended as a spray pot mum.

1 Drawing Sheet

The present invention comprises a new and distinct cultivar of chrysanthemum, botanically known as *Dendranthema grandiflora*, and referred to by the cultivar name Red Akron.

Red Akron, identified as 4120 (91–413B05), is a product of a mutation induction program. The new cultivar was discovered and selected by inventor Cornelis P. VandenBerg on Jan. 25, 1994 in a controlled environment in Salinas, Cailf. as one flowering plant within a flowering block established as rooted cuttings from stock plants which had been exposed as unrooted cuttings to an X-ray source of 1750 rads in Fort Myers, Fla. on Aug. 5, 1993. The irradiated parent cultivar was the cultivar Akron, disclosed in U.S. Plant Pat. No. 9,105, and described as a flat daisy spray pot mum with a red-purple ray floret color.

The irradiation program resulting in Red Akron had as its primary objective the expansion of color ranges of the parent cultivar. The irradiation program comprised irradiation of cuttings of the parent cultivar at irradiation levels of 1500, 1750 and 2000 rads. A total of 2,113 cuttings harvested from a total of 225 irradiated plants were planted on Nov. 22, 1993. Of these, 12 initial selections were made, which selections were then revegetated and reflowered. Three consecutive flowerings resulted in discarding 9 of the original selections on Sep. 30, 1994. The 3 remaining selections were maintained as PIs (Possible Introductions) and further trailed in Salinas, Cailf. and Leamington, Ontario, Canada, ultimately resulting in the decision to introduce one selection as Red Akron, and one selection as Plum Akron, the latter being disclosed in pending application ser. No. 08/786,421; the one remaining selection was maintained for further trialing.

The first act of asexual reproduction of Red Akron was accomplished when vegetative cuttings were taken from the initial selection in April of 1994 in a controlled environment in Salinas, Cailf., by technicians working under supervision of Cornelis P. VandenBerg.

Horticultural examination of controlled flowerings of successive plantings has shown that the unique combination of characteristics as herein disclosed for Red Akron are firmly fixed and are retained through successive generations of asexual reproduction.

Red Akron has not been observed under all possible environmental conditions. The phenotype may vary significantly with variations in environment such as temperature, light intensity and daylength, without, however, any variance in genotype.

The following observations, measurements and comparisons describe plants grown in Salinas, Cailf., and in Leamington, Ontario, Canada, under greenhouse conditions which approximate those generally used in commerical greenhouse practice.

The following traits have been repeatedly observed and are determined to be basic characteristics of Red Akron, which, in combination, distinguish this Chrysanthemum as a new and distinct cultivar:

1. Flat capitulm form.
2. Daisy capitulm type.
3. Dark red ray floret color.

4. Diameter across face of capitulm of 64 to 76 mm when fully opened, when grown as a pinched spray pot mum.

5. Photoperiodic flowering response of 50 to 56 days after start of short days.

6. Plant height, with 14 to 16 long days after sticking unrooted cuttings and with 1 to 2 applications of 2500 ppm B-9 SP ranges from 20 to 30 cm when grown as a pinched pot mum with 4 cuttings in a 15 cm pot.

7. Branching pattern is spreading and prolific, each plant developing 4 to 6 laterals after pinch.

8. Recommended as a spray pot mum.

The accompanying photographic drawing is a side view of Red Akron, grown as a spray pot mum with 4 cuttings in a 15 cm pot, with the colors being as nearly true as possible with illustrations of this type.

Of the commercial cultivars known to the inventor, the most similar in comparison to Red Akron is the parent cultivar Akron. All traits of Red Akron are similar to those of Akron, except for the ray floret color. The ray floret color of Red Akron is described as dark (R.H.S. 46A), while the ray floret color of Akron is described as red-purple (R.H.S. 71B).Red Akron also differs from sibling cultivar Plum Akron only with respect to ray floret color, with the color of Plum Akron being red-purple compared to the deep red ray floret color of Red Akron.

In the following description color references are made to The Royal Horticultural Society Colour Chart. The color values were determined on plant material grown as a pinched pot mum with 4 cuttings in a 15 cm pot in Salinas, Cailf. on Aug. 30, 1996.

Classification:

*Botanical.*—*Dendranthema grandiflora*cv Red Akron.

*Commercial.*—Flat daisy spray pot mum.

Inflorescence

Capitulum:

*Form.*—Flat.

*Type.*—Daisy.

*Diameter across face.*—64 to 76 mm when fully opened.

Corolla of ray florets:

*Color (general tonality from a distance of three meters).*—Dark red.

*Color (upper surface).*—46A.

*Color (under surface).*—42A to 42B.

*Shape.*—Straight, flat, rounded ray floret tip.

C. Corolla of disc florets:

*Color (mature).*—14B.

*Color (immature).*—144A.

D. Reproductive organs:

*Androecium.*—Present on disc florets only; moderate pollen.

*Gynoecium.*—Present on both ray and disc florets.

Plant

A. General appearance:

*Height.*—20 to 30 cm when grown as a pinched pot mum with 14 to 16 long days after sticking unrooted cuttings prior to start of short days and 1 to 2 applications of 2500 ppm B-9 SP.

*Branching pattern.*—Spreading and prolific, with 4 to 6 laterals developing after pinch.

A. Foliage:

*Color. (upper surface).*—147A.

*Color. (under surface).*—147B.

*Shape.*—Deeply lobed and strongly serrated.

What is claimed is:

1. A new and distinct Chrysanthemum plant named Red Akron, as described and illustrated.

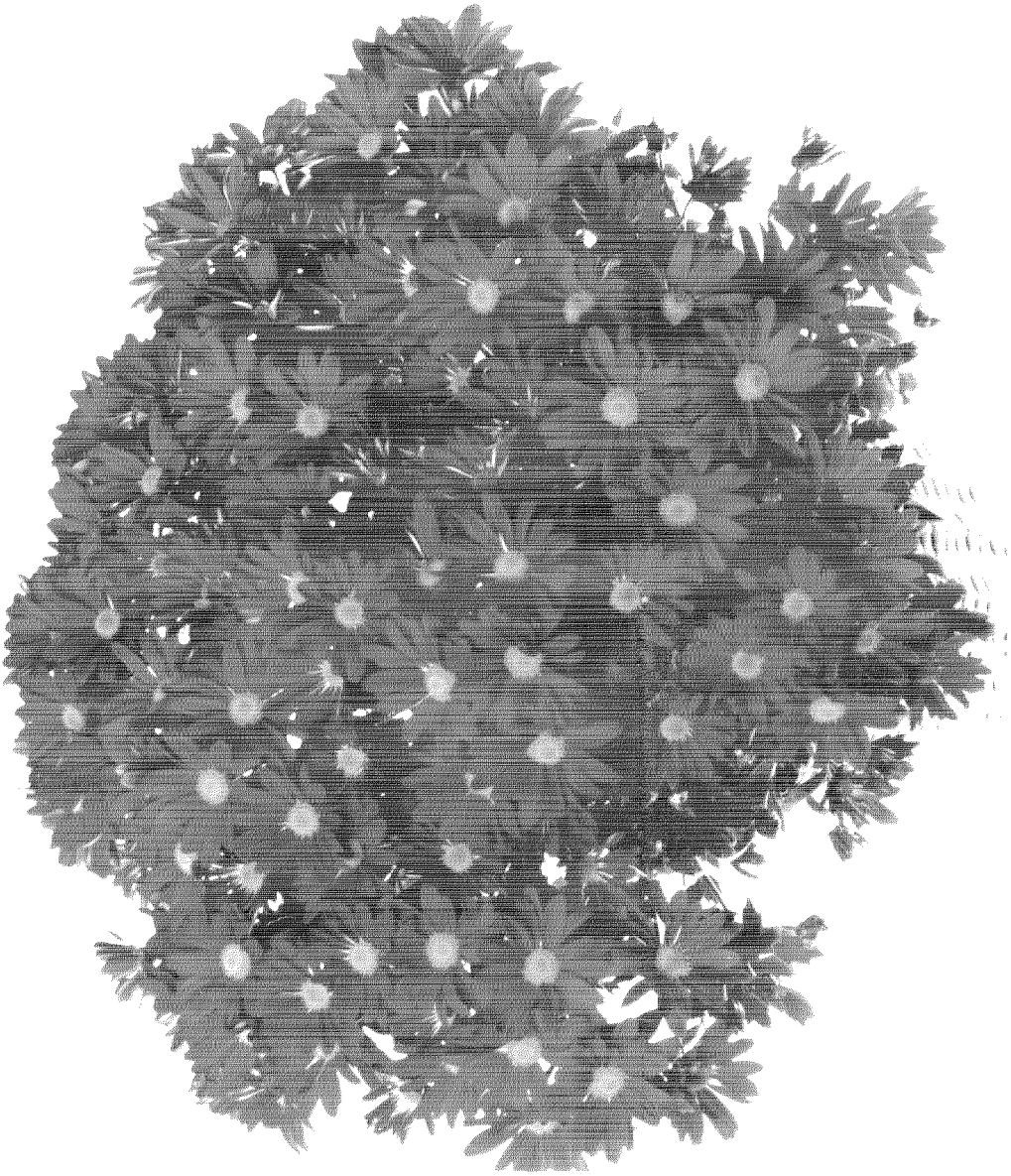

* * * * *